US00PP24610P3

(12) United States Plant Patent

Hamilton et al.

(10) Patent No.: US PP24,610 P3

(45) Date of Patent: Jul. 8, 2014

(54) RASPBERRY PLANT NAMED 'DRISRASPFIVE'

(50) Latin Name: ***Rubus idaeus* L.**
Varietal Denomination: DrisRaspFive

(75) Inventors: Brian K. Hamilton, Richmond, TX (US); Carlos D. Fear, West Malling (GB); Marta C. Baptista, Tavira (PT)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 95 days.

(21) Appl. No.: 13/507,921

(22) Filed: Aug. 7, 2012

(65) Prior Publication Data

US 2014/0047594 P1 Feb. 13, 2014

(51) Int. Cl.
*A01H 5/00* (2006.01)

(52) U.S. Cl.
USPC ..... Plt./204; Plt./203

(58) Field of Classification Search
USPC ..... Plt./203, 204
See application file for complete search history.

*Primary Examiner* — Susan McCormick Ewoldt

(74) *Attorney, Agent, or Firm* — Jondle Plant Sciences Division of Swanson & Bratschun, L.L.C.

(57) ABSTRACT

A new and distinct variety of raspberry plant named 'DrisRaspFive' particularly distinguished by having high yield, good flavor, and dark red berries, is disclosed.

2 Drawing Sheets

Genus and species: *Rubus idaeus* L.
Variety denomination: 'DrisRaspFive'.

BACKGROUND OF THE NEW PLANT

The present invention relates to a new and distinct raspberry variety designated 'DrisRaspFive' and botanically known as *Rubus idaeus* L. This new raspberry variety was discovered in Santa Cruz, Calif. in August 2003 and originated from a cross between the proprietary female parent raspberry plant 'Driscoll Maravilla' (U.S. Plant Pat. No. 14,804) and the proprietary male parent raspberry plant 'DrisRaspFour' (U.S. Plant Pat. No. 22,731). The original seedling of the new variety was first asexually propagated at a nursery in Santa Cruz, Calif. 'DrisRaspFive' was subsequently asexually propagated and underwent further testing at a nursery in Kent, United Kingdom for eight years. The present invention has been found to be stable and reproduce true to type through successive asexual propagations via tissue culture and root cuttings.

Plant Breeder's Rights for this variety have not been applied for. 'DrisRaspFive' has not been made publicly available or sold more than one year prior to the filing date of this application.

SUMMARY OF THE INVENTION

The following are the most outstanding and distinguishing characteristics of this new variety when grown under normal horticultural practices in Kent, United Kingdom:

1. High yield;
2. Good flavor; and
3. Dark red berries.

DESCRIPTION OF THE PHOTOGRAPHS

This new raspberry plant is illustrated by the accompanying photographs which show fruit of the plant as well as the primocanes. The colors shown are as true as can be reasonably obtained by conventional photographic procedures. The photographs are of plants that are six to eighteen months old.

DESCRIPTION OF THE NEW VARIETY

Figure 1:
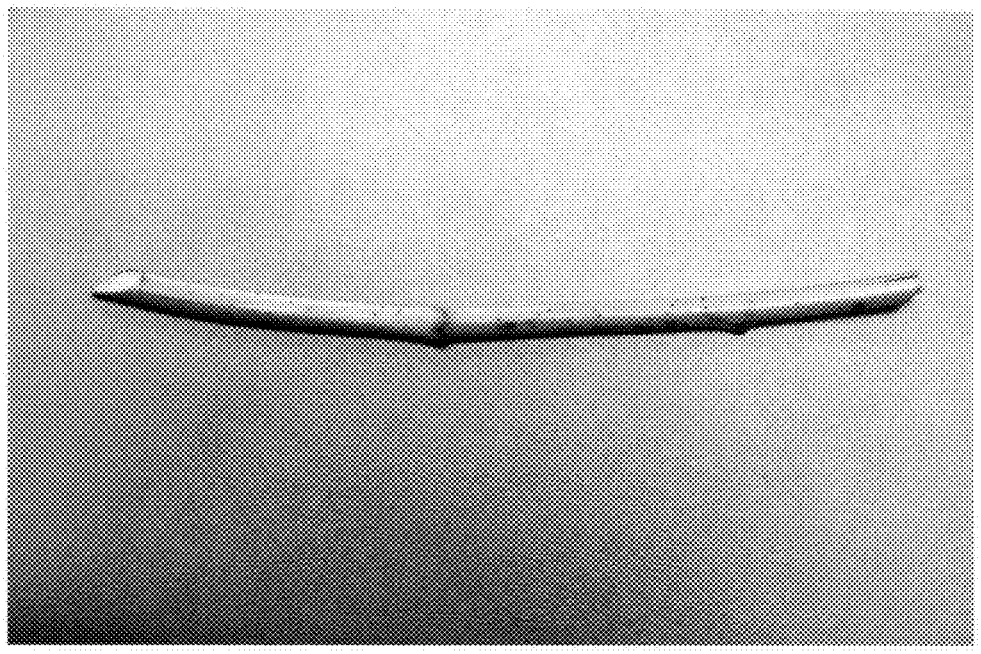
FIG. 1 shows a section of a young cane with prickles.
Figure 2:
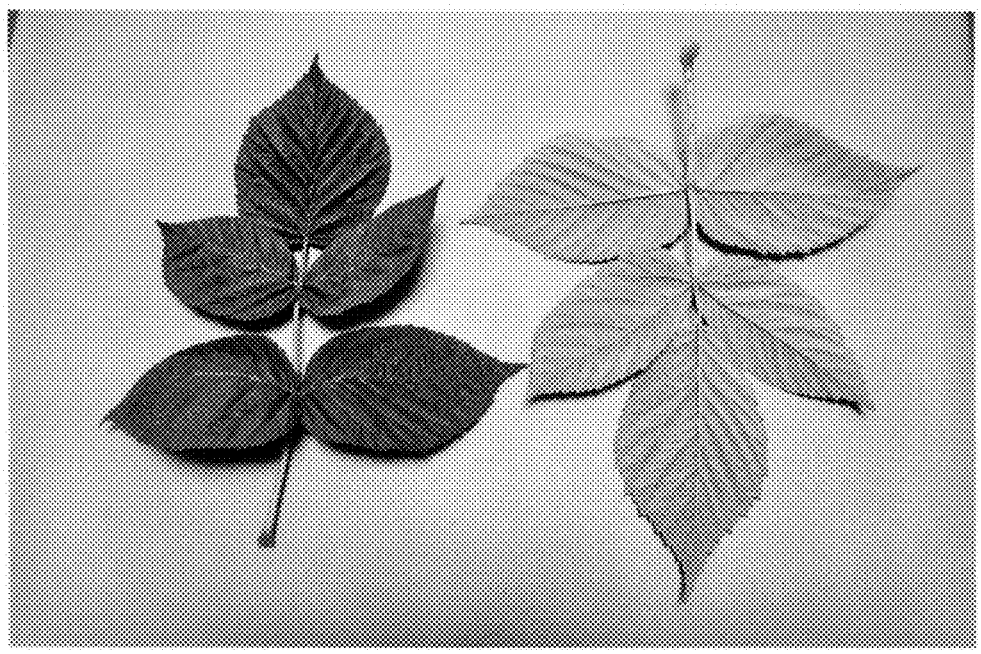
FIG. 2 shows both the upper surface and the lower surface of the plant leaves.
Figure 3:
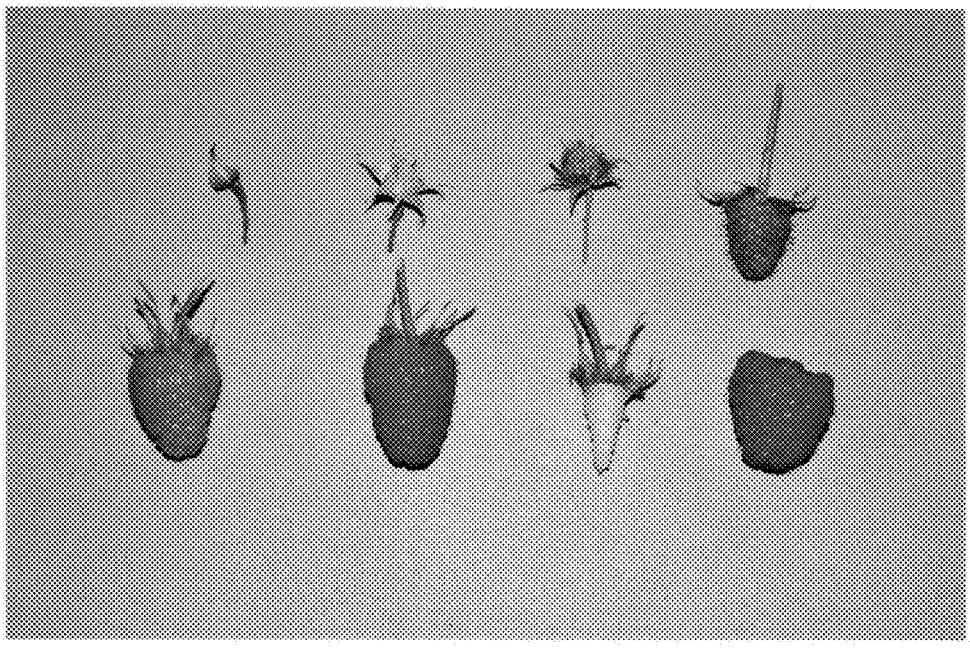
FIG. 3 shows close-up views of typical flowers and fruit at various stages of development.

The following detailed descriptions set forth the distinctive characteristics of 'DrisRaspFive'. The data which define these characteristics is based on observations taken in Kent, United Kingdom from 2005 to 2012. This description is in accordance with UPOV terminology. Color designations, color descriptions, and other phenotypical descriptions may deviate from the stated values and descriptions depending upon variation in environmental, seasonal, climatic and cultural conditions. 'DrisRaspFive' has not been observed under all possible environmental conditions. The botanical description of 'DrisRaspFive' was taken from six to eighteen-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family*.—Rosaceae.
*Botanical*.—*Rubus idaeus* L.
*Common name*.—Raspberry.
*Variety name*.—'DrisRaspFive'.

Parentage:

*Female parent*.—The proprietary raspberry plant 'Driscoll Maravilla' (U.S. Plant Pat. No. 14,804).

*Male parent*.—The proprietary raspberry plant 'Dris-RaspFour' (U.S. Plant Pat. No. 22,731).

Plant:

*Propagation*.—Tissue culture and root cuttings.

*Size*.—Medium.

*Height*.—22.4 cm.

*Width*.—13.0 cm.

*Length/width ratio*.—1.7.

*Productivity*.—High.

*Self-fruitfulness*.—Self-fruitful.

*New cane growth habit*.—Erect or upright.

Primocanes:

*Number of canes*.—Medium.

*Glaucosity (waxy bloom) on full grown shoot after picking*.—Medium.

*Cane length*.—Medium.

*Cane length for current season's cane in autumn*.—82.06 cm.

*Length of internode*.—Medium.

*Internodal distance at central ⅓ of cane*.—5.85 cm.

*Length of vegetative bud*.—Short.

*Number of young shoots*.—Few.

*Anthocyanin coloration of apex during rapid growth*.—Present.

*Intensity of anthocyanin coloration of apex during rapid growth*.—Weak.

*Time of young shoot emergence from the soil*.—Medium.

*Time of beginning of flowers*.—Medium.

*Time of beginning of fruit ripening in autumn*.—Medium.

*Length of fruiting period in autumn*.—Medium.

*Percent of cane flowering as primocane*.—65%.

*Percent primocane yield of total yield*.—50%.

*Glaucosity (waxy bloom) on current years cane in autumn*.—Medium.

*Cane strength*.—Strong.

*Shape of cane cross section*.—Rounded.

*Pubescence on canes*.—Present.

Floricanes:

*Dormant cane length in summer*.—Medium (Pruned).

*Dormant cane color in summer*.—RHS N187A (Dark greyed-purple).

*Fruiting lateral attitude*.—Erect.

*Time of vegetative bud burst*.—Late February.

*Time of beginning of flowers*.—Early April.

*Time of beginning of fruit ripening*.—Early May.

*Length of fruiting period*.—Early May to mid-August.

Prickles (spines):

*Density of spines on central third*.—Medium.

*Size of base of prickles*.—Small.

*Length (from base to tip)*.—Short; 1.8 mm.

*Color (pigmentation)*.—RHS 178A (Dark greyed-red).

*Attitude of tip*.—Horizontal.

*Size*.—Large.

*Texture*.—Soft.

*Presence and distribution on petioles*.—Present and regularly distributed.

Leaves:

*Terminal leaflet*.—Length: Long; 14.08 cm. Width: Broad; 11.84 cm. Length/width ratio: 1.2. Leaf color: Upper surface: RHS 137A (Dark green). Lower surface: RHS 148B (Medium yellow-green). Profile in cross section: Flat (straight). Relief between the veins: Strong. Overlapping of leaflets: Free. Glossiness: Medium. Shape: Ovate. Apex: Acuminate. Base: Obtuse. Margin: Crenate. Arrangement: Simple.

*Lateral leaflets (basal pair)*.—Number of leaflets: Usually 5. Size: Length: 11.37 cm. Width: 7.58 cm. Length/width ratio: 1.5. Arrangement: Compound-opposite. Shape: Ovate. Apex: Acuminate. Base: Obtuse. Margin: Crenate. Lateral leaflet (length to stalklet, lower pair): Short.

*Rachis length between terminal leaflet and adjacent lateral leaflets*.—4.5 mm.

*Petiole*.—Size: Length: 6.1 mm. Diameter: 1.79 mm. Pigmentation: Upper surface: RHS 144C (Light yellow-green). Lower surface: RHS 144C (Light yellow-green).

Stipules:

*Orientation*.—Erect.

Flowers:

*Size*.—Large.

*Diameter*.—3.30 cm.

*Petal length*.—0.91 cm.

*Petal width*.—0.46 cm.

*Length/width ratio*.—2.0.

*Flowering period*.—Primocane: Medium; Early June to mid-September. Floricane: Medium; Mid-June to late July.

*Pedicel*.—Number of spines: Few. Anthocyanin coloration: Absent. Length: Long; 3.17 cm. Diameter: 0.74 mm.

Peduncle:

*Presence of anthocyanin coloration*.—Absent.

*Intensity of anthocyanin coloration*.—Absent or very weak.

Fruit:

*Length*.—Long; 3.02 cm.

*Width*.—Broad; 2.77 cm.

*Ratio of length to width*.—1.1, as long as broad.

*Average number of drupelets per fruit*.—98.

*Weight (g/fruit)*.—Primocane: 6.5. Floricane: 5.7.

*Soluble solids (% in Brix)*.—10.7.

*Titratable acidity (% as citric acid)*.—10.6.

*Weight of seeds (g/seed)*.—0.165.

*Size*.—From medium to large.

*Shape*.—Ovate (broad conical).

*Size of single drupelet*.—Medium.

*Color*.—Immature fruit: RHS 43B (Light red). Maturing fruit: RHS 45A (Medium red). Mature fruit color: RHS 46A (Dark red).

*Glossiness*.—Medium.

*Firmness*.—Medium.

*Adherence to plug*.—Medium.

*Main bearing type*.—Both on previous years cane in summer and on current years cane in autumn.

*Time of ripening*.—Primocane: Medium. Floricane: Early April.

*Harvest season*.—Primocane: Early August to late October. Floricane: Mid-June to late July.

*Yield*.—High.

Pest and disease resistance: Not tested.

COMPARISON WITH PARENTAL AND COMMERCIAL VARIETIES

'DrisRaspFive' differs from the proprietary female parent 'Driscoll Maravilla' (U.S. Plant Pat. No. 14,804) in that 'DrisRaspFive' has terminal leaflets with strong relief between the veins, an obtuse base and a crenate margin, whereas 'Driscoll Maravilla' has terminal leaflets with medium relief between the veins, a round to cordate base and a doubly serrate margin. Additionally, 'DrisRaspFive' has fruit that is less firm than 'Driscoll Maravilla'.

'DrisRaspFive' differs from the proprietary male parent 'DrisRaspFour' (U.S. Plant Pat. No. 22,731) in that 'DrisRaspFive' has a medium number of strong primocanes with medium internode length, whereas 'DrisRaspFour' has many, medium strength primocanes with long internode length. Additionally, 'DrisRaspFive' has less dense spines than 'DrisRaspFour'.

'DrisRaspFive' differs from commercial variety 'Driscoll Cardinal' (U.S. Plant Pat. No. 14,903) in that 'DrisRaspFive' has a strong primocanes with few young shoots, whereas 'Driscoll Cardinal' has medium strength primocanes with many young shoots. Additionally, 'DrisRaspFive' has fruit that is medium glossy, whereas 'Driscoll Cardinal' has fruit that is weakly glossy.

We claim:

1. A new and distinct variety of raspberry plant named 'DrisRaspFive' as described and shown herein.

* * * * *